US011278510B2

(12) United States Patent
Pinoie et al.

(10) Patent No.: US 11,278,510 B2
(45) Date of Patent: Mar. 22, 2022

(54) PARENTERAL NUTRITION FORMULATION WITH OPTIMIZED AMINO ACID AND GLUCOSE CONTENT

(71) Applicants: BAXTER INTERNATIONAL INC., Deerfield, IL (US); BAXTER HEALTHCARE SA, Glattpark (CH)

(72) Inventors: Vanja Pinoie, Sint-Genesius-Rode (BE); Preeti Sharma, Brussels (BE); Julianna Roth Jakubowski, Chicago, IL (US); Mary Hise Brown, Vernon Hills, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 150 days.

(21) Appl. No.: 16/562,014

(22) Filed: Sep. 5, 2019

(65) Prior Publication Data

US 2021/0069138 A1 Mar. 11, 2021

(51) Int. Cl.
| | |
|---|---|
| *A61K 31/198* | (2006.01) |
| *A23L 33/175* | (2016.01) |
| *A23L 33/125* | (2016.01) |
| *A61J 1/12* | (2006.01) |
| *A61K 9/00* | (2006.01) |
| *A61K 31/401* | (2006.01) |
| *A61K 31/405* | (2006.01) |
| *A61K 31/4172* | (2006.01) |
| *A61K 31/721* | (2006.01) |
| *A61K 33/06* | (2006.01) |
| *A61K 45/06* | (2006.01) |

(52) U.S. Cl.
CPC .......... *A61K 31/198* (2013.01); *A23L 33/125* (2016.08); *A23L 33/175* (2016.08); *A61J 1/12* (2013.01); *A61K 9/0029* (2013.01); *A61K 31/401* (2013.01); *A61K 31/405* (2013.01); *A61K 31/4172* (2013.01); *A61K 31/721* (2013.01); *A61K 33/06* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 7,770,611 | B2 * | 8/2010 | Houwaert | ............. A61J 1/2093 141/114 |
| 2010/0317602 | A1 | 12/2010 | Moore | |
| 2012/0205673 | A1 | 8/2012 | Park et al. | |
| 2014/0205673 | A1 | 7/2014 | Abele et al. | |

FOREIGN PATENT DOCUMENTS

| | | | | |
|---|---|---|---|---|
| CN | 103610693 | | 3/2014 | |
| EP | 2 135 604 A | * | 12/2009 | ........... A61K 31/198 |
| EP | 2135604 | | 12/2009 | |
| JP | 2005220105 | | 8/2005 | |
| JP | 2005330244 | | 12/2005 | |

OTHER PUBLICATIONS

Stein (GMS German Medical Science, 7:1-8, 2009) (Year: 2009).*
Madsen et al (Practical Gastroenterology, pp. 46-68, Jul. 2006) (Year: 2006).*
ISR and Written Opinion for App. No. PCT/US2020/049485 dated Dec. 14, 2020 (15 pages).
"Comparison of osmolality of solutions used in parenteral nutrition"; Detolle S. et al.; Elsevier Science Publishers, Amsterdam, NL 1988 and Annales Pharmaceutiques Francaises 1988 FR, vol. 46, No. 1, 1988, pp. 7-14 ISSN: 0003-4509.
Hoffer, Leonard John, "Parenteral Nutrition: Amino Acids," Nutrients, 2017, 9, 257 (10 pages).
Weijs et al., "Protein Intake, Nutritional Status and Outcomes in ICU Survivors: A Single Center Cohort Study; Journal of Clinical Medicine," 2019 (9 pages).
Boullata et al., "A.S.P.E.N. Clinical Guidelines: Parenteral Nutrition Ordering, Order Review, Compounding, Labeling, and Dispensing," vol. 38, No. 3, Mar. 2014; pp. 334-377.
Gupta et al., "Patent protection strategies," J Pharm Bioallied Sci. Jan.-Mar. 2010; 2(1): 2-7; pp. 1-13.
Kingley, Jodi, "Fluid and Electrolyte Management in Parenteral Nutrition," Support Line, Dec. 2005, vol. 27, No. 6, (8 pages).
Lee et al., "Higher dextrose delivery via TPN related to the development of hyperglycemia in non-diabetic critically ill patients," Nutrition Research and Practice 2011; 5(5):450-454.
"Appropriate Dosing for Parenteral Nutrition: Aspen Recommendations," Jan. 8, 2019; (3 pages).
Bonaterra et al., "Krill oil-in-water emulsions protects against lipopolysaccharides-induced proinflammatory activation of macrophages in vitro," Marine Drugs (2017), 15:74.
Driscoll, "Pharmaceutical and Clinical Aspects of Lipid Injectable Emulsions," Journal of Parenteral and Enteral Nutrition, 2017, 41, 125-134.
Calder et al., "Lipid emulsions in parenteral nutrition of intensive care patients: current thinking and future directions," Intensive Care Medicine, 2010, 36(5), 735-749.
Fell et al., "Intravenous Lipid Emulsions in Parenteral Nutrition," Advances in Nutrition, 2015, 6(5), 600-610.
Written Opinion of the International Preliminary Examining Authority for PCT/US2020/049485 dated May 17, 2021 (7 pages).

* cited by examiner

*Primary Examiner* — Craig D Ricci
(74) *Attorney, Agent, or Firm* — K&L Gates LLP

(57) ABSTRACT

The present disclosure relates to a sterile medical product for parenteral nutrition comprising a polymeric container having at least a first and a second chamber which are separated by a non-permanent peel seal, wherein the first chamber contains a composition of amino acids and optionally electrolytes, and wherein the second chamber contains a dextrose solution, and wherein the product is characterized by a high protein (nitrogen) content per volume. The reconstituted solution is configured to be administered peripherally or centrally for the treatment of patients suffering from malnutrition and/or having a need for increased uptake of amino acids.

18 Claims, 1 Drawing Sheet

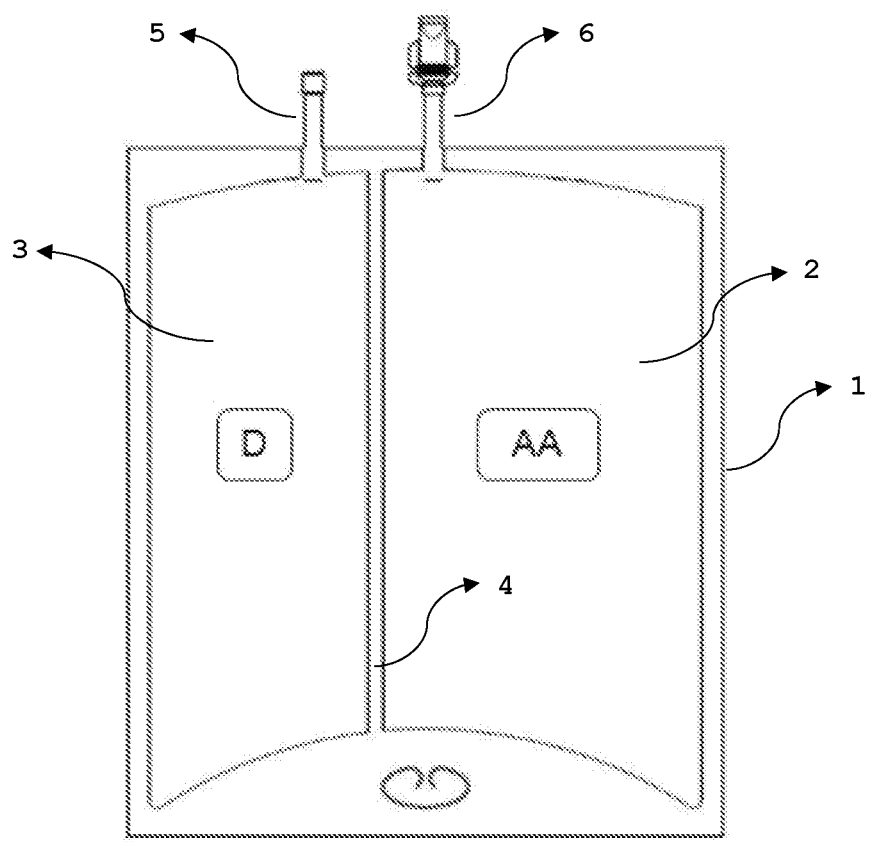

PARENTERAL NUTRITION FORMULATION WITH OPTIMIZED AMINO ACID AND GLUCOSE CONTENT

TECHNICAL FIELD

The present disclosure relates to a sterile medical product for parenteral nutrition comprising a polymeric container having at least a first and a second chamber which are separated by a non-permanent peel seal, wherein the first chamber contains a composition of amino acids and optionally electrolytes, and wherein the second chamber contains a dextrose solution, and wherein the product is characterized by a high protein (nitrogen) content per volume. The reconstituted solution is configured to be administered peripherally or centrally for the treatment of patients suffering from malnutrition and/or having a need for increased uptake of amino acids.

DESCRIPTION OF THE RELATED ART

Products for parenteral administration comprising amino acids, electrolytes and dextrose, provided in a dual chamber container are known in the art and are also available on the market. The products are generally indicated as a caloric component in a parenteral nutrition regimen and as a source for nitrogen.

For example, Clinimix and Clinimix E are well-known products from Baxter. These parenteral nutrition products consist of dual chamber containers having a first chamber comprising an amino acid formulation which in case of Clinimix E in addition contains various electrolytes, and a second chamber which contains a dextrose solution and calcium chloride. The total nitrogen content in the reconstituted solution of various Clinimix products ranges from 4.54 g/L to a maximum of 8.26 g/L of the solution. The dextrose content in the reconstituted solution ranges between 25 g/L and 50 g/L.

Similar compositions have been described, for example, in JP 2005330244 A, which describes a composition for peripheral intravenous infusion provided in a dual chamber container and which comprises amino acids, calcium, phosphoric acid and potassium in a first chamber and a carbohydrate formulation comprising also phosphoric acid, potassium, but no calcium, in a second chamber, and which after mixing has a pH of 6.3-7.4. The solution further contains vitamins in the amino acid chamber.

CN 103610693 A also describes a dual chamber container wherein a first chamber comprises an amino acid composition, wherein 200 ml of the amino acid formulation contain 1.120 g of isoleucine, 1.240 g of alanine, 0.260 g of tryptophane, 2.500 g of leucine, 0.660 g of valine, 2.480 g of lysine acetate, 0.760 g of aspartic acid, 1.580 g of arginine, 0.700 g of methionine, 2.40 g of glycine, 1.200 g of histidine, 1.870 g of phenylalanine, 0.200 g of cysteine, 0.440 g of serine, 1.300 g of threonine, 1.300 g of glutamic acid and 0.070 g of tyrosine, and 50-200 ppm silver ions; the second chamber comprises 800 ml of a 15% glucose solution which further contains inorganic salts, specifically 120.0 g anhydrous glucose, 2.920 g sodium chloride, 2.160 g potassium acetate, 1.088 g potassium dihydrogen phosphate, 0.740 g magnesium sulfate, 1.792 g calcium gluconate and 5.752 mg zinc sulfate ($ZnSO_4.7H_2O$).

JP 2005220105 describes a peripheral intravenous nutrition infusion preparation wherein a sugar, an amino acid and an electrolyte are compounded and has a final pH of 6.8-7.6 and a sugar concentration of 2-5 w/v-%. The preparation is provided in a dual chamber container, wherein a first chamber contains the sugar and the electrolyte and a second chamber contains the amino acid.

EP 2135604 A1 discloses an infusion solution for nutrition for use with cancer patients and which is characterized by being a low-sugar, high-amino acid infusion. Specifically, the composition contains high levels of L-glutamine or glycine and up to 50 g/L of glucose.

US 2010317602 A1 discloses a sterile aqueous composition for parenteral administration and use with intradialytic patients comprising between 2 and 26 g of dextrose per 450 ml, and between 12 and 45 g of amino acids per 450 ml of solution.

US 20120205673 A1 describes a three-chamber container with a high amino-acid, low-lipid and low-carbohydrate parenteral nutrition solution for administration to obese patients.

While certain combinations of amino acid and carbohydrate formulations for parenteral nutrition are known already, as described above, improved products for addressing specifically the needs of acutely hospitalized patients are required, as dietary protein and energy deficit are still common in said patients and universally in critical illness. Such products should address such nutritional deficiencies which can otherwise lead to protein-energy malnutrition, the most prominent features of which are generalized muscle atrophy and fat loss. Importantly, said muscle atrophy is much more dangerous than fat loss, since it is life-threatening, debilitating and difficult to reverse once the patients are able to leave the ICU or hospital. In contrast, the average patient today has adequate or even more than adequate fat reserves in cases of hypocaloric nutrition (Hoffer: Parenteral Nutrition: Amino Acids, Nutrients 2017, 9, 257). The present invention therefore strives to provide for an improved composition for parenteral nutrition which optimally balances the protein (amino acid) and carbohydrate content for addressing the above challenges in parenteral nutrition of critically ill patients. Specifically, the formulation according to the invention is designed to deliver a very high amount of protein in a given fluid volume, while it also provides for very low levels of glucose so as to avoid hyperglycemia. The formulation thus provides for an exceptionally high and novel protein/calorie ratio which so far has not been made available in any formulation before.

SUMMARY

It is an object of the present invention to provide a medical product for parenteral nutrition comprising a polymeric container having a first and second chamber which are separated by a non-permanent peel seal, wherein the first chamber contains an amino acid formulation and optionally additionally contains electrolytes, and wherein the second chamber comprises a dextrose formulation and optionally additionally contains calcium. The medical products for parenteral nutrition are configured to be used for central or peripheral administration to a patient in need. They are further configured to provide parenteral nutrition with a high protein (amino acid) content per volume to patients whose alimentary tract cannot be used, and/or whose gastrointestinal absorption of protein is impaired, and/or whose metabolic requirements for protein are increased, wherein the ratio of protein/calorie is very high in comparison to known formulations based on amino acids and carbohydrates.

Accordingly, while the protein content of the formulation according to the invention is increased to address issues of protein malnutrition, such as muscular atrophy, the dextrose content of the product is lowered in comparison to prior art compositions to avoid or reduce the critical aspects connected with the administration of high amounts of carbohydrate to a patient, such as hyperglycemia. The medical product is thus configured to optimally balance the amount of nitrogen and carbohydrate to be delivered to a patient in a given volume of parenteral nutrition solution.

According to a first aspect of the invention, the first chamber of the medical product contains an amino acid formulation comprising 23.29-28.47 g/L L-alanine, 12.94-15.82 g/L L-arginine, 11.58-14.16 g/L glycine, 5.40-6.60 g/L L-histidine, 6.75-8.24 g/L L-isoleucine, 8.22-10.04 g/L L-leucine, 6.53-7.98 g/L L-lysine, 4.50-5.50 g/L L-methionine, 6.30-7.70 g/L L-phenylalanine, 7.65-9.35 g/L L-proline, 5.63-6.88 g/L L-serine, 4.72-5.77 g/L L-threonine, 2.02-2.47 g/L L-tryptophan, 0.45-0.54 g/L L-tyrosine, and 6.53-7.98 g/L L-valine, but does not contain any electrolytes.

According to a second aspect of the invention, the first chamber further comprises electrolytes.

According to a third aspect of the invention, the first chamber further comprises 49.0-60.0 mEq/L sodium, 3.67-4.49 g/L potassium dihydrogen phosphate, 7.0-9.0 mEq/L magnesium, 103.0-155.0 mEq/L acetate, and 5.9-7.2 g/L chloride.

According to a fourth aspect, the second chamber of the medical product contains a dextrose formulation, wherein the dextrose is present in a concentration of from 26.6 wt.-% and 41.0 wt.-%.

According to a fifth aspect, the second chamber contains a dextrose formulation comprising dextrose in a concentration of from 26.6 wt.-% to 29.4 wt.-%.

According to a sixth aspect, the second chamber contains a dextrose formulation comprising dextrose in a concentration of from 37.1 wt.-% to 41.0 wt.-%.

According to a seventh aspect, the second chamber further contains calcium in a concentration of from 11 to 14 mEq/L.

According to an eighth aspect, the formulation reconstituted from the first and the second chamber comprises 14.41-18.72 g/L L-alanine, 8.01-10.40 g/L L-arginine, 7.17-9.31 g/L glycine, 3.34-4.34 g/L L-histidine, 4.17-5.42 g/L L-isoleucine, 5.08-6.60 g/L L-leucine, 4.04-5.25 g/L L-lysine, 2.78-3.61 g/L L-methionine, 3.90-5.06 g/L L-phenylalanine, 4.73-6.14 g/L L-proline, 3.48-4.52 g/L L-serine, 2.92-3.80 g/L L-threonine, 1.25-1.62 g/L L-tryptophan, 0.28-0.36 g/L L-tyrosine, 4.04-5.25 g/L L-valine, 12.9-15.2 wt.-% dextrose, 30-40 mEq/L sodium, 2.3-2.9 g/L potassium phosphate dibasic, 4.0-6.0 mEq/L magnesium, 64.0-102.0 mEq/L acetate, 3.9-5.0 g/L chloride, and 3.9-5.1 mEq/L calcium.

According to a ninth aspect, the formulation reconstituted from the first and the second chamber comprises 14.41-18.72 g/L L-alanine, 8.01-10.40 g/L L-arginine, 7.17-9.31 g/L glycine, 3.34-4.34 g/L L-histidine, 4.17-5.42 g/L L-isoleucine, 5.08-6.60 g/L L-leucine, 4.04-5.25 g/L L-lysine, 2.78-3.61 g/L L-methionine, 3.90-5.06 g/L phenylalanine, 4.73-6.14 g/L L-proline, 3.48-4.52 g/L L-serine, 2.92-3.80 g/L L-threonine, 1.25-1.62 g/L L-tryptophan, 0.28-0.36 g/L L-tyrosine, 4.04-5.25 g/L L-valine, and from 12.9 to 15.2 wt.-% dextrose.

According to a tenth aspect, the formulation reconstituted from the first and the second chamber comprises 14.41-18.72 g/L L-alanine, 8.01-10.40 g/L L-arginine, 7.17-9.31 g/L glycine, 3.34-4.34 g/L L-histidine, 4.17-5.42 g/L L-isoleucine, 5.08-6.60 g/L L-leucine, 4.04-5.25 g/L L-lysine, 2.78-3.61 g/L L-methionine, 3.90-5.06 g/L L-phenylalanine, 4.73-6.14 g/L L-proline, 3.48-4.52 g/L L-serine, 2.92-3.80 g/L L-threonine, 1.25-1.62 g/L L-tryptophan, 0.28-0.36 g/L L-tyrosine, 4.04-5.25 g/L L-valine, 9.3-10.9 wt.-% dextrose, 30-40 mEq/L sodium, 2.3-2.9 g/L potassium dihydrogen phosphate, 4.0-6.0 mEq/L magnesium, 64.0-102.0 mEq/L acetate, 3.9-5.0 g/L chloride, and 3.9-5.1 mEq/L calcium.

According to an eleventh aspect, the formulation reconstituted from the first and the second chamber comprises 14.41-18.72 g/L L-alanine, 8.01-10.40 g/L L-arginine, 7.17-9.31 g/L glycine, 3.34-4.34 g/L L-histidine, 4.17-5.42 g/L L-isoleucine, 5.08-6.60 g/L L-leucine, 4.04-5.25 g/L L-lysine, 2.78-3.61 g/L L-methionine, 3.90-5.06 g/L L-phenylalanine, 4.73-6.14 g/L L-proline, 3.48-4.52 g/L L-serine, 2.92-3.80 g/L L-threonine, 1.25-1.62 g/L L-tryptophan, 0.28-0.36 g/L L-tyrosine, 4.04-5.25 g/L L-valine, and from 9.3 wt.-% to 10.9 wt.-% dextrose.

According to a twelfth aspect, the formulation reconstituted from the first and second chamber has a total calorie content of from 717 Kcal/L to 878 Kcal/L, specifically of from 795 to 800 Kcal/L, and more specifically of 797 Kcal/L.

According to a thirteenth aspect, the formulation reconstituted from the first and second chamber has a total calorie content of from 595 Kcal/L to 732 Kcal/L, specifically of from 660 to 665 Kcal/L, and more specifically of 663 Kcal/L.

According to a fourteenth aspect, the formulation reconstituted from the first and second chamber has a total nitrogen content of from 11.5 g/L to 14.9 g/L, specifically of from 12.9 to 13.5 g/L, and more specifically of 13.2 g/L.

According to a fifteenth aspect, the first chamber of the medical product contains an amino acid formulation comprising 18.63-22.78 g/L L-alanine, 10.35-12.65 g/L L-arginine, 9.27-11.33 g/L glycine, 4.32-5.28 g/L L-histidine, 5.40-6.60 g/L L-isoleucine, 6.57-8.03 g/L L-leucine, 5.22-6.39 g/L L-lysine, 3.60-4.40 g/L L-methionine, 5.04-6.16 g/L L-phenylalanine, 6.12-7.48 g/L L-proline, 4.50-5.50 g/L L-serine, 3.78-4.62 g/L L-threonine, 1.62-1.98 g/L L-tryptophan, 0.36-0.44 g/L L-tyrosine, and 5.22-6.38 g/L L-valine, and the second chamber comprises a dextrose formulation in a concentration of from 11.9 wt.-% to 13.1 wt.-%.

According to a sixteenth aspect, the formulation reconstituted from the first and the second chamber comprises 10.8-14.04 g/L L-alanine, 6.01-7.80 g/L L-arginine, 5.38-6.98 g/L glycine, 2.50-3.25 g/L L-histidine, 3.13-4.07 g/L L-isoleucine, 3.81-4.95 g/L L-leucine, 3.03-3.94 g/L L-lysine, 2.09-2.71 g/L L-methionine, 2.92-3.80 g/L L-phenylalanine, 3.55-4.61 g/L L-proline, 2.61-3.39 g/L L-serine, 2.19-2.85 g/L L-threonine, 0.94-1.22 g/L L-tryptophan, 0.21-0.27 g/L L-tyrosine, 3.03-3.93 g/L L-valine, and 4.6-5.4 wt.-% dextrose.

According to a seventeenth aspect of the invention, the formulation reconstituted from the first and second chamber has a total calorie content of from 365 Kcal/L to 455 Kcal/L, specifically of from 405 to 415 Kcal/L, and more specifically of 410 Kcal/L.

According to an eighteenth aspect, the formulation reconstituted from the first and second chamber has a total nitrogen content of from 8.6 g/L to 11.2 g/L, specifically of from 9.5 to 10.0 g/L, and more specifically of 9.9 g/L.

According to a nineteenth aspect, the formulation reconstituted from the first and second chamber comprises 16.56 g/L L-alanine, 9.20 g/L L-arginine, 8.24 g/L glycine, 3.84 g/L L-histidine, 4.80 g/L L-isoleucine, 5.84 g/L L-leucine, 4.64 g/L L-lysine, 3.20 g/L L-methionine, 4.48 g/L L-phenylalanine, 5.44 g/L L-proline, 4.00 g/L L-serine, 3.36 g/L L-threonine, 1.44 g/L L-tryptophan, 0.32 g/L L-tyrosine, and 4.64 g/L L-valine.

According to a twentieth aspect, the formulation reconstituted from the first and second chamber comprises 2.61 g/L potassium dihydrogen phosphate, 2.05 g/L sodium chloride, 0.51 g/L magnesium chloride, and 0.33 g/L calcium chloride dehydrate.

According to a twenty-first aspect, the formulation reconstituted from the first and second chamber comprises dextrose in a concentration of 14 g/100 mL (140 g/L).

According to a twenty-second aspect, the formulation reconstituted from the first and second chamber comprises dextrose in a concentration of 10 g/100 mL (100 g/L).

According to a twenty-third aspect, the formulation reconstituted from the first and second chamber comprises amino acids in a concentration of 8 g/100 mL (80 g/L).

According to a twenty-third aspect, the formulation reconstituted from the first and second chamber comprises nitrogen in a concentration of 1320 mg/100 mL (13.20 g/L).

According to a twenty-fourth aspect, the formulation reconstituted from the first and second chamber comprises 35 mEq/L sodium, 30 mEq/L potassium, 5 mEq/L magnesium, 4.5 mEq/L calcium, 83 mEq/L acetate, 76 mEq/L chloride, and 30 mEq/L phosphate ($HPO_4^{2-}$).

According to a twenty-fifth aspect, the formulation reconstituted from the first and second chamber comprises 71 mEq/L acetate and 32 mEq/L chloride.

According to a twenty-sixth aspect, the formulation reconstituted from the first and second chamber comprises 16.56 g/L L-alanine, 9.20 g/L L-arginine, 8.24 g/L glycine, 3.84 g/L L-histidine, 4.80 g/L L-isoleucine, 5.84 g/L L-leucine, 4.64 g/L L-lysine, 3.20 g/L L-methionine, 4.48 g/L L-phenylalanine, 5.44 g/L L-proline, 4.00 g/L L-serine, 3.36 g/L L-threonine, 1.44 g/L L-tryptophan, 0.32 g/L L-tyrosine, 4.64 g/L L-valine, 35 mEq/L sodium, 30 mEq/L potassium, 5 mEq/L magnesium, 4.5 mEq/L calcium, 83 mEq/L acetate, 76 mEq/L chloride, 30 mEq/L phosphate ($HPO_4^{2-}$), and 100 g/L dextrose.

According to a twenty-seventh aspect, the formulation reconstituted from the first and second chamber comprises 16.56 g/L L-alanine, 9.20 g/L L-arginine, 8.24 g/L glycine, 3.84 g/L L-histidine, 4.80 g/L L-isoleucine, 5.84 g/L L-leucine, 4.64 g/L L-lysine, 3.20 g/L L-methionine, 4.48 g/L L-phenylalanine, 5.44 g/L L-proline, 4.00 g/L L-serine, 3.36 g/L L-threonine, 1.44 g/L L-tryptophan, 0.32 g/L L-tyrosine, 4.64 g/L L-valine, 35 mEq/L sodium, 30 mEq/L potassium, 5 mEq/L magnesium, 4.5 mEq/L calcium, 83 mEq/L acetate, 76 mEq/L chloride, 30 mEq/L phosphate ($HPO_4^{2-}$), and 140 g/L dextrose.

According to a twenty-eighth aspect, the formulation reconstituted from the first and second chamber comprises 16.56 g/L L-alanine, 9.20 g/L L-arginine, 8.24 g/L glycine, 3.84 g/L L-histidine, 4.80 g/L L-isoleucine, 5.84 g/L L-leucine, 4.64 g/L L-lysine, 3.20 g/L L-methionine, 4.48 g/L L-phenylalanine, 5.44 g/L L-proline, 4.00 g/L L-serine, 3.36 g/L L-threonine, 1.44 g/L L-tryptophan, 0.32 g/L L-tyrosine, 4.64 g/L L-valine, 71 mEq/L acetate, 32 mEq/L chloride, and 100 g/L dextrose.

According to a twenty-ninth aspect, the formulation reconstituted from the first and second chamber comprises 16.56 g/L L-alanine, 9.20 g/L L-arginine, 8.24 g/L glycine, 3.84 g/L L-histidine, 4.80 g/L L-isoleucine, 5.84 g/L L-leucine, 4.64 g/L L-lysine, 3.20 g/L L-methionine, 4.48 g/L L-phenylalanine, 5.44 g/L L-proline, 4.00 g/L L-serine, 3.36 g/L L-threonine, 1.44 g/L L-tryptophan, 0.32 g/L L-tyrosine, 4.64 g/L L-valine, 71 mEq/L acetate, 32 mEq/L chloride, and 140 g/L dextrose.

According to a thirtieth aspect, the formulation reconstituted from the first and second chamber comprises 12.24 g/L L-alanine, 6.90 g/L L-arginine, 6.18 g/L glycine, 2.88 g/L L-histidine, 3.60 g/L L-isoleucine, 4.38 g/L L-leucine, 3.48 g/L L-lysine, 2.40 g/L L-methionine, 3.36 g/L L-phenylalanine, 4.08 g/L L-proline, 3.00 g/L L-serine, 2.52 g/L L-threonine, 1.08 g/L L-tryptophan, 0.24 g/L L-tyrosine, and 3.48 g/L L-valine.

According to a thirty-first aspect, the formulation reconstituted from the first and second chamber comprises 12.24 g/L L-alanine, 6.90 g/L L-arginine, 6.18 g/L glycine, 2.88 g/L L-histidine, 3.60 g/L L-isoleucine, 4.38 g/L L-leucine, 3.48 g/L L-lysine, 2.40 g/L L-methionine, 3.36 g/L L-phenylalanine, 4.08 g/L L-proline, 3.00 g/L L-serine, 2.52 g/L L-threonine, 1.08 g/L L-tryptophan, 0.24 g/L L-tyrosine, 3.48 g/L L-valine, and 5 g/100 mL (50 g/L) dextrose.

According to a thirty-second aspect, the formulation reconstituted from the first and second chamber comprises 12.24 g/L L-alanine, 6.90 g/L L-arginine, 6.18 g/L glycine, 2.88 g/L L-histidine, 3.60 g/L L-isoleucine, 4.38 g/L L-leucine, 3.48 g/L L-lysine, 2.40 g/L L-methionine, 3.36 g/L L-phenylalanine, 4.08 g/L L-proline, 3.00 g/L L-serine, 2.52 g/L L-threonine, 1.08 g/L L-tryptophan, 0.24 g/L L-tyrosine, 3.48 g/L L-valine, 53 mEq/L acetate, 24 mEq/L chloride, and 5 g/100 mL (50 g/L) dextrose.

According to a thirty-third aspect, the formulation reconstituted from the first and second chamber has a pH of from 4.5 to 7.0.

According to a thirty-fourth aspect, the formulation reconstituted from the first and second chamber has a pH of 7.0.

According to a thirty-fifth aspect, the product according to the invention has a protein/glucose ratio of 0.57.

According to a thirty-sixth aspect, the product according to the invention has a protein/glucose ratio of 0.8.

According to a thirty-seventh aspect, the product according to the invention has a protein/glucose ratio of 1.2.

According to a thirty-eighth aspect, the product further comprises a third chamber which contains a lipid emulsion.

BRIEF DESCRIPTION OF THE DRAWINGS

FIG. 1 shows a schematic drawing of a medical product according to the invention, comprising a polymeric container (1) having a first chamber (2) and a second chamber (3) which are separated by a non-permanent peel seal (4) which can be broken upon applying mechanical pressure. The container (1) further comprises an injection port (5) on the second chamber and an administration port (6) on the first chamber. "D" represents dextrose, "AA" represents amino acids. In certain configurations of the present invention, the AA chamber is larger than the D chamber, as shown in this FIG. 1. The ratio between AA chamber and D chamber generally is from 1.4:1 to 1.9:1, and preferably is from 1.5:1 to 1.8:1.

DEFINITIONS

"Central parenteral nutrition (CPN)" refers to parenteral nutrition when administered via a central vein to infuse nutrients at high concentrations and in a smaller volume. Catheters are usually inserted into the superior vena cava, or, alternatively, the inferior vena cava. CPN allows repeated access to the venous system for prolonged times.

"Critical illness" refers to a life-threatening multisystem process that can result in significant morbidity or mortality, often preceded by a period of physiological deterioration. Critically ill patients, for example, suffer from muscle wasting due to loss of nitrogen and reduced exogenous amino acid deposition into endogenous proteins (Weijs et al., J Clin Med 2019, 8, 43)

"Dextrose" is interchangeably used herein with the expression "glucose". Dextrose concentration is provided herein in %, which refers to the grams of dextrose per 100 mL of fluid. A 5% dextrose solution contains 5 grams of dextrose per 100 mL of fluid (0.05 gram/ml).

"Electrolytes" as used herein refers to compounds or substances that dissociate in the solution to release positively and negatively charged ions that can carry electric current. Specifically, the term refers to such electrolytes which are essential minerals found in the body. Primary ions of electrolytes are sodium ($Na^+$), potassium ($K^+$), calcium ($Ca^{2+}$), magnesium ($Mg^{2+}$), chloride ($Cl^-$), hydrogen phosphate ($HPO_4^{2-}$), and hydrogen carbonate ($HCO_3^-$).

"Hyperglycemia" as used herein refers to a condition in which an excessive amount of glucose circulates in the blood plasma. This is generally a blood sugar level higher than 11.1 mmol/l (200 mg/dl), but symptoms may not start to become noticeable until even higher values such as 15-20 mmol/l (~250-300 mg/dl).

"Hypervolemia" as used herein refers to an excessive blood volume, wherein mean systemic circulatory pressure is high, causing a net fluid loss into the interstitium resulting in some edema formation. The causes of hypervolemia can be complex and include renal failure, congestive heart failure, or liver failure, especially when these conditions are associated with overzealous fluid administration. The expression "fluid overload" more generally refers to excess total body water content associated with edema.

"mEq" as used herein refers to the unit of measurement used for sodium, chloride, potassium, magnesium, calcium, and acetate in IV fluids and PN, while the millimole (mM) or the milliequivalent is used for phosphorus. A mEq measures chemical-combining capacity, or the number of electrolyte atoms that will combine with 1 mEq of another electrolyte. mEq can be calculated from milligrams using the following formula: mEq=(mg×valence)/atomic weight. Phosphorus is measured in millimoles because at a physiologic pH of 7.4, the phosphate ion exists partly in divalent and partly in monovalent forms. The ratio is 4 mM of hydrogen phosphate (divalent, $HPO_4^{2-}$) to 1 mM of dihydrogen phosphate (monovalent, $H_2PO_4^-$).

"Overfeeding" as used herein refers to the provision of one or more of the nutrients components of parenteral nutrition in an amount or at a rate that exceeds the physiologic utilization and excretion of the nutrient.

"Parenteral nutrition" (PN) as used herein refers to the intravenous administration of nutritional components, which may include protein, carbohydrate, fat, minerals and electrolytes, vitamins and trace elements, to patients who cannot eat or absorb enough food through tube (enteral) feeding to maintain good nutrition status. Diseases and conditions where PN is indicated include but are not limited to short bowel syndrome, GI fistulas, bowel obstruction, critically ill patients, and severe acute pancreatitis. Patients receiving PN include pre-term or newborn babies, infants, children and adults.

"Parenteral nutrition solution" as used herein refers to a sterile liquid chemical formula suitable for parenteral nutrition and which is given directly into the bloodstream of a patient through an intravenous (IV) catheter.

"Peripheral parenteral nutrition (PPN)" as used herein refers to the administration of PN solution via a cannula inserted into peripheral vein. The term "peripheral" refers to superficial veins, most often of the upper extremities. PPN is indicated, for example, for short-term PN, when catheterization of a central vein is contraindicated or impossible, in case of catheter sepsis or bacteremia.

"Reconstitution" as used herein refers to the mixing of fluids contained in distinct chambers within a multi-chamber bag by opening or breaking one or more nonpermanent (peel) seals which separate the chambers and the fluids contained therein. A "reconstituted" fluid thus is a fluid which is obtained by mixing two or more fluids located in different chambers of a multi-chamber bag. Such reconstitution is generally done shortly before administration of the reconstituted fluid to a patient.

"Total parenteral nutrition (TPN)" as used herein implies that all macronutrient (carbohydrate, nitrogen and lipid) and micronutrient (vitamins, trace elements and minerals) and fluid requirements of a patient are met by an intravenous nutrient solution and no significant nutrition is obtained from other sources.

DETAILED DESCRIPTION

For several decades, it has been consensus that critically ill patients have an increased protein requirement. However, until recently, clinical nutrition has mostly focused on the benefits of calorie supplementation, whereas the importance of protein/amino acid supplementation was not adequately addressed. PN's advantage in this regard is the ability to deliver a substantial dose of amino acids very promptly. Care must be taken, of course, to avoid protein overprovision, which can go along with, for example, hyperammonemia in liver dysfunction or other urea cycle disorders. Concerns relating to PN also encompass an inadvertent caloric overfeeding and hyperglycemia. Hyperglycemia in hospitalized patients is associated with a higher risk of complications and death, especially when no insulin therapy is used (Lee et al: Higher dextrose delivery via TPN related to the development of hyperglycemia in non-diabetic critically ill patients. Nutr Res Pract 2011, 5, 450-454). Until recently, there was a lack of high-protein, energy-restricted enteral nutrition (EN) products, and most standard premix PN products delivered too much energy, volume, or both to be recommendable or practical in critical illness (Hoffer, Nutrients 2017, 9, 257). Generally, excess glucose, lipids and calories from TPN can cause many complications, such as hepatobiliary alterations, the above-mentioned hyperglycemia and hypertriglyceridemia.

The present invention has been made, therefore, under the hypothesis that a high-protein (about 2 g/kg per day), hypocaloric nutrition is an important step towards improving clinical outcomes in catabolic critical illness.

An important objective of parenteral nutrition (PN), in addition to meeting energy requirements, is to maintain vital organ structure and function. Protein is provided in PN for the maintenance of cell structure, tissue repair, immune defense and skeletal muscle mass. Generally, protein synthesis should be promoted. In PN, protein is generally delivered in the form of amino acid solutions, a physiologic mixture of essential and nonessential amino acids, the concentration and composition of can vary quite considerably.

Amino acids (AA), the building blocks in protein synthesis, are classified as nonessential, essential, and conditionally nonessential AA and their precursors (Table 1), see Stein et al.: Amino Acids—Guidelines on Parenteral Nutrition, Chapter 4, GMS German Medical Science 2009, 7, 1612.

TABLE 1

Classification of amino acids as dispensable,
indispensable and conditionally dispensable

| Nonessential AA | Essential AA | Conditionally Essential AA (Precursors) |
|---|---|---|
| Isoleucine | Alanine | Arginine (Glutamate, Aspartic Acid) |
| Leucine | Aspartic Acid | Cysteine (Glutamic Acid, Serine) |
| Lysine | Asparagine | Glutamine (Glutamic Acid, Ammonia) |
| Methionine | Glutamic Acid | Histidine (Serine, Choline) |
| Phenylalanine | Glycine | Serine (Glutamate) |
| Threonine | Proline | Tyrosine (Phenylalanine) |
| Tryptophan | | |
| Valine | | |

Recommendations such as provided by the American Society for Parenteral and Enteral Nutrition, ASPEN, (2019), cover general ranges for certain diseases and clinical conditions and encompass recommendations for the uptake in g/kg/d for protein/amino acid, and further recommend a range for dextrose administration in PN (mg/kg/min), as well as standard daily requirements for electrolytes and minerals, vitamins and trace elements, respectively. For example, the guidelines recommend 0.8-1.5 g/kg/d of protein/amino acids for stable patients, 1.2-2.5 g/kg/d for critically ill, trauma and sepsis patients, and 1.5-2 g/kg/d for patients with burns (see also Weijs et al. 2019). Dosings are also recommended.

Despite associated risks when overdosed, carbohydrates are important in PN, as they are the primary energy source for the human body. Especially the brain and neural tissue, erythrocytes, leukocytes, the lens of the eye exclusively require glucose or use glucose preferentially.

So, in the light of the general ASPEN recommendations, it remains a challenge to design an optimal ready-to-use PN product which provides an optimized, increased protein/amino acid content selected from the broader range suggested in the guidelines, including an optimal choice and ratio of and between the individual amino acids, and balancing the protein/amino acid content against the energy needs of the patients, in terms of glucose, by providing an optimal combination with dextrose and, optionally, electrolytes.

In addition, it is an important aspect in the design of such product to provide the said amino acids and dextrose in an optimal volume, as maintaining an appropriate water balance is crucial for optimal metabolic function. During periods of acute illness, ADH and aldosterone production are often increased. Hypotension, stress, decreased intravascular volume, pain, surgery, and increased plasma osmolality all increase ADH output, favoring water retention. Aldosterone production increases when kidney perfusion decreases, causing sodium and water retention (Kingley, Fluid and Electrolyte Management in Parenteral Nutrition, Support Line 2005, 27, 6). For example, an aging individual, generally defined as older than 65 years, has a diminished ability to adjust to hemodynamic changes compared with a younger person. During illness, intravenous (IV) fluids are a relevant source of additional fluid which influences the water balance of a patient.

The present invention, therefore, also seeks to provide a high protein/amino acid in less fluid than in prior art formulations. The volumes of the medical product in question are 2500 mL of reconstituted solution or less. According to one aspect of the invention, the reconstituted volume of the medical product is 2000 mL or less. In specific embodiments of the present invention, the reconstituted volumes are 2000 mL, 1500 mL or 1000 mL.

Further, the present invention seeks to provide such optimized product comprising at least a carbohydrate formulation and an amino acid combination, wherein the product is further configured to be administered through a large-diameter central vein or configured to be administered into a peripheral vein. Central access allows for the use of highly concentrated, hypertonic solutions, and are often used for patients requiring PN for more than 2 weeks. Either a temporary central venous catheter (CVC) or long-term CVC, such as a tunneled catheter, an implanted port, or a peripherally inserted central catheter (PICC) can be used. As CVCs can increase catheter-related blood stream infections, peripheral parenteral nutrition (PPN) is used where indicated and possible. Because PPN is administered into a peripheral vein, the osmolarity of a PPN solution must be adjusted to lower concentrations in order to avoid vein damage and thrombophlebitis. PPN are often lipid-based, but in the present invention it was the goal to also provide the above benefits of a high-protein hypocaloric solution for PPN according to the invention, even though lipids are not an essential part of the formulation and are preferably not contained.

In the prior art, PN products are provided which comprise amino acids, lipids and carbohydrates. They are often provided in 3-chamber bags, side-by-side, wherein the lipids, carbohydrates and amino acids can be admixed before administration by breaking non-permanent peel seals between the respective chambers. Electrolytes can also be contained in the nutrition solutions. Trace elements and vitamins are added to the parenteral nutrition solutions before administration or are administered separately from the parenteral nutrition. The lipids are a concentrated source of energy which are provided as oil-in-water emulsions ranging from 10% to 30%. However, lipids can and are often infused separately, especially when patients have a high protein and/or minimal fluid need and do not have increases energy needs. Accordingly, it is one aspect of the present invention to provide for a product for central or peripheral administration which is preferably comprised of an amino acid formulation, which may additionally also comprise electrolytes, and a carbohydrate formulation, which preferably comprises dextrose and optionally calcium. According to another aspect of the invention, the product does not comprise a lipid formulation, even though such lipid formulation can be combined with the amino acid and carbohydrate formulation in a product (then comprising three chambers) or can be added before administration or can be provided separately from the administration of the medical product according to the invention.

According to one aspect, the medical product of the invention consists of a two-chamber container, wherein the first chamber comprises the amino acid solution according to the invention, and the second chamber comprises the carbohydrate solution according to the invention. The medical product may also comprise a third chamber which comprises a lipid emulsion.

The medical product of the invention accordingly comprises a multi-chambered container, wherein at least two chambers are individually arranged. In a general embodiment, the said container includes at least a first chamber and a second chamber, but may optionally have additional chambers, such as a third chamber, a fourth chamber or a fifth chamber. According to one embodiment, the medical product of the invention contains two chambers, that is a first and a second chamber. According to another embodiment, the medical product of the invention contains three chambers. The medical product of the invention is further characterized by peelable seals which separate the respective chambers from each other. For example, the first chamber is separated by the second chamber by a peelable seal located in between the chambers. If a third chamber is present, it is also separated from the first and/or the second chamber by a peelable seal. If more than one peelable seal is present, e.g. in a three-chamber container, the peelable seals are preferably independently openable by selective pressure to a selected chamber. Other than between the respective chambers, the chambers are surrounded by permanent seals. The permanent seals can have various shapes, such as a curved shape on the upper and lower end of the chambers as shown in FIG. 1. Such curved shape supports an easy and efficient drainage of the reconstituted solution from the container and for provides for a stable hanger opening. As shown in FIG. 1 for a two-chamber or dual chamber container (1), a first (2) and a second (3) chamber are vertically arranged and separated by a peelable seal (4). The peelable seal can extend over the full length of the weld seam which is longitudinally arranged between the chambers. Alternatively, only a portion of the weld seam can be designed as a peelable seal. By pressurizing chambers (1 and 2) containing the formulation to be mixed together before administration to a patient, a user or care giver can prepare a reconstituted formulation from individually stored components of chambers according to the invention.

As illustrated in FIG. 1, the container (1) can further include an administration tube (6) in fluid communication with the first chamber (2) and a medication tube (5) in fluid communication with the second chamber (3). Medication tube (5) provides communication with the interior of chamber (3) and can be equipped with a seal such as a septum that allows components such as a liquid to be added to or removed into or from Chamber (3) or the container after the contents of chambers (2) and (3) have been mixed. The tube (6) can also include a membrane that seals shut the tube (6) and can be pierced by, for example, a cannula or spike of an administration set. The tube (6) can be sealed until the time to access the contents of the container (1). A peelable safety seal can surround an opening of the tube (6).

In one embodiment, the container can further include one or more tubes in fluid communication with the first and second or any additional chamber. The tubes can provide communication with the interior of, for example, chambers (2) and (3) according to the invention and allow components such as solutions according to the invention to be added to or removed from chambers (2) and (3). For example, the tubes can be used as fill ports for chambers (2) and (3) or as additive ports to allow addition of a medication or other additive to one of the chambers after the chamber has been filled and sealed. The tubes can also be capped or sealed after the chambers (2) and (3) have been filled with the desired components. The number, size, and dimensions of the filling tube(s), medication tube (5), and administration tube (6) can vary depending on the application.

The container and the peelable seals such as peelable seal (4) in FIG. 1 can be constructed from films able to make peal seal layers in accordance with embodiments of the present disclosure. The peelable seal layer films can allow both peelable and permanent seals to be created. Thus, the permanent side seals as well as the peelable seals can be created from the same layer of film.

The containers can be made principally of flexible polymeric materials, although the container could include non-polymeric materials such as metal foils without departing from the disclosure. Numerous polymeric films have been developed for use in containers. Suitable films may be of a monolayer structure or a multiple layer structure. The monolayer structure can be made from a single polymer, or from a polymer blend. The multiple layer structures can include layers such as a solution contact layer, a scratch resistant layer, a barrier layer for preventing permeation of gas (such as carbon dioxide, oxygen or water vapor), tie layers, or other layers. It is also contemplated to use more than one web of film for one or both sidewalls. Appropriate polymeric materials are generally selected from homopolymers and copolymers of polyolefins, polyamides, polyesters, polybutadiene, styrene and hydrocarbon copolymers, polyimides, polyester-polyethers, polyamide-polyethers to name a few. It is preferably to use non-PVC materials for the primary packaging, including the film and the port tubes as well as the twist-off protector. According to one embodiment of the invention, the film of the primary packaging of the medical product of the invention is a four-layer co-extruded film prepared from poly(cyclohexylenedimethylene)cyclohexane dicarboxylate copolymer (PCCE) (outer layer), maleic anhydride modified poly(ethylene vinyl acetate) (tie layer), poly (ethylene vinyl acetate) (EVA) (inside layer), and poly (ethylene-propylene) copolymer (PP/PE) and styrene-ethylene-butylene-styrene block polymer (SEBS) (sealant layer). According to another embodiment, the port tube(s) are polyolefin-based, three layered, co-extruded components which are PVC free. The outer layer is prepared from a blend of PP/PE and SEBS, the middle layer from a blend of SEBS, EVA, PP and PE, and the inner layer from EVA. The middle layer is optional and can basically be replaced with a virtual layer consisting of the same material as the outer layer. According to yet another aspect of the invention, the TOP can be made from a blend of PP, EVA SEBS and optionally comprise a color, such as, for example, Polybatch® Blue. The TOP preferably is PVC-free.

The seal layer for the container of the product of the invention should display bi-modal behavior. What is meant by bi-modal behavior is that the material is capable of forming a permanent seal under one set of sealing or manufacturing conditions and a peelable seal at a second set of sealing or manufacturing conditions. The seal layer can be a homophase polymer, or a matrix-phase polymer system. Suitable homophase polymers include polyolefins and polypropylene, specifically a propylene and ethylene copolymer.

According to one embodiment of the invention, the product according to the invention has a first and a second chamber. According to one embodiment, the chambers are designed to contain fluids which upon reconstitution result in a volume of from 0.8 to 2.2 L. Preferably, the resulting volume after reconstitution is from 1.0 to 2.0 L, specifically the resulting volume of the reconstituted solution is 1.0, 1.5 or 2.0 L. Obviously, the volumes of the first and the second chamber can vary so as to result in the above disclosed final reconstituted volumes. Preferred embodiments encompass a volume, of the first chamber comprising an amino acid formulation, which is larger than the volume of the glucose formulation in the second chamber.

For reconstituted formulations, which are suitable for central administration, the volume of the final, reconstituted formulation is from about 0.8 to 1.2 L, for example 1.0 L. Typical volumes of the amino acid formulation of products for central administration thus are from 600 to 700 ml and, typical volumes of the glucose formulation are from 300 to 400 ml, respectively.

In case of a product according to the invention which is intended for peripheral administration, the final, reconstituted volume is from 1.8 to 2.2 L, for example 2.0 L. Typical volumes of the amino acid formulation of products for peripheral administration thus are from 1200 to 1300 ml and, typical volumes of the glucose formulation are from 700 to 800 ml, respectively.

According to one embodiment, the first chamber of a product for central administration contains an amino acid formulation comprising about

| | |
|---|---|
| 23.29-28.47 g/L | L-Alanine, |
| 12.94-15.82 g/L | L-Arginine, |
| 11.58-14.16 g/L | Glycine, |
| 5.40-6.60 g/L | L-Histidine, |
| 6.75-8.24 g/L | L-Isoleucine, |
| 8.22-10.04 g/L | L-Leucine, |
| 6.53-7.98 g/L | L-Lysine, |
| 4.50-5.50 g/L | L-Methionine, |
| 6.30-7.70 g/L | L-Phenylalanine, |
| 7.65-9.35 g/L | L-Proline, |
| 5.63-6.88 g/L | L-Serine, |
| 4.72-5.77 g/L | L-Threonine, |
| 2.02-2.47 g/L | L-Tryptophan, |
| 0.45-0.54 g/L | L-Tyrosine, and |
| 6.53-7.98 g/L | L-Valine. |

According to one embodiment, the amino acid concentration in the first chamber is from 12.0 to 13%, and preferably it is 12.5%. Percentages are given in g/100 ml.

The second chamber of a product for central administration according to the invention contains a glucose (dextrose) formulation, wherein dextrose is contained in the formulation in a concentration of between 26.6% to 41.0%.

According to one embodiment, dextrose is contained in a concentration of from 37.1-41.0%, for example dextrose is contained in a concentration of 39%. According to another embodiment, dextrose is contained in a concentration of from 26.6% to 29.4%, preferably it is 28%.

The amino acid formulation of a product for central administration according to the invention may further comprise electrolytes, including, but not limited to, sodium, potassium, phosphate, magnesium, acetate, and chloride, and optionally also vitamins and/or trace elements. Vitamins and/or trace elements can also be added to the product before administration to the patient. In such case, said vitamins and/or trace elements are added to the reconstituted solution immediately before the solution is infused into the patient.

Electrolytes may be contained in the amino acid formulation of the product for central administration, for example, in an amount of about

| | |
|---|---|
| 49.0-60.0 mEq/L | sodium |
| 3.67-4.49 g/L | potassium hydrogen phosphate |
| 7.0-9.0 mEq/L | magnesium |
| 103.0-155.0 mEq/L | acetate, and |
| 5.9-7.2 g/L | chloride. |

According to what is disclosed herein, the above formulations contained in the first and the second chamber can be mixed or reconstituted by breaking the peelable seal between the chambers. The reconstituted solution for central parenteral nutrition thus comprises, according to one embodiment,

| | |
|---|---|
| 14.41-18.72 g/L | L-Alanine, |
| 8.01-10.40 g/L | L-Arginine, |
| 7.17-9.31 g/L | Glycine, |
| 3.34-4.34 g/L | L-Histidine, |
| 4.17-5.42 g/L | L-Isoleucine, |
| 5.08-6.60 g/L | L-Leucine, |
| 4.04-5.25 g/L | L-Lysine, |
| 2.78-3.61 g/L | L-Methionine, |
| 3.90-5.06 g/L | L-Phenylalanine, |
| 4.73-6.14 g/L | L-Proline, |
| 3.48-4.52 g/L | L-Serine, |
| 2.92-3.80 g/L | L-Threonine, |
| 1.25-1.62 g/L | L-Tryptophan, |
| 0.28-0.36 g/L | L-Tyrosine, and |
| 4.04-5.25 g/L | L-Valine. |

The reconstituted solution further comprises dextrose in a concentration of from 12.9& to 15.2%, or comprises dextrose in a concentration of from 9.3% to 10.9%.

Accordingly, it is one aspect of the present invention to provide for a PN solution for central administration wherein the ratio of the concentration (%) of amino acids to dextrose is about 8:10. According to another aspect, the ratio of amino acid to dextrose concentration (%) is about 8:14.

According to another embodiment, if electrolytes are contained in the amino acid formulation for central administration according to the invention, the reconstituted solution further comprises 30-40 mEq/L sodium, 2.3-2.9 g/L potassium phosphate dibasic, 4-6 mEq/L magnesium, 64-102 mEq/L acetate, and 3.9-5.0 g/L chloride.

According to yet another embodiment, where the dextrose solution of the product for central administration comprises calcium, the reconstituted solution comprises 3.9-5.1 mEq/L calcium.

It is one aspect of the present invention to keep the amount of acetate and chloride low. As the formulation according to the invention aims at increasing the amino acid concentration, the reconstituted solutions for central administration further comprise acetate and chloride, which should be generally be present in low amounts. According to one embodiment, acetate is contained in an amount of from 64 mEq/L and 102 mEq/L. For example, in a reconstituted solution for central administration without electrolytes, the solution contains about 71 mEq/L acetate.

According to another embodiment, a formulation for peripheral administration is provided, which has an optimized amino acid composition and an optimized ratio of amino acid and dextrose concentration.

According to one embodiment, the first chamber of a product for peripheral administration contains an amino acid formulation comprising about

| | |
|---|---|
| 18.63-22.78 g/L | L-Alanine, |
| 10.35-12.65 g/L | L-Arginine, |
| 9.27-11.33 g/L | Glycine, |
| 4.32-5.28 g/L | L-Histidine, |
| 5.40-6.60 g/L | L-Isoleucine, |
| 6.57-8.03 g/L | L-Leucine, |
| 5.22-6.39 g/L | L-Lysine, |
| 3.60-4.40 g/L | L-Methionine, |
| 5.04-6.16 g/L | L-Phenylalanine, |
| 6.12-7.48 g/L | L-Proline, |
| 4.50-5.50 g/L | L-Serine, |
| 3.78-4.62 g/L | L-Threonine, |
| 1.62-1.98 g/L | L-Tryptophan, |
| 0.36-0.44 g/L | L-Tyrosine, and |
| 5.22-6.38 g/L | L-Valine. |

According to one embodiment, the amino acid concentration in the said first chamber is from 9.0 to 11.0%. For example, the amino acid concentration is 10.0%. Percentages are given in g/100 ml. According to one embodiment, the chamber comprising the said amino acid formulation has a volume of 600 ml.

The second chamber of a product for peripheral administration according to the invention contains a glucose (dextrose) formulation, wherein dextrose is contained in the formulation in a concentration of between 11.9% to 13.1%. For example, the dextrose concentration is 12.5%. According to one embodiment, the chamber comprising the said glucose formulation has a volume of 400 ml.

The amino acid formulation of a product for peripheral administration according to the invention may further comprise electrolytes, including, but not limited to, sodium, potassium, phosphate, magnesium, acetate, and chloride, and optionally also vitamins and/or trace elements. Vitamins and/or trace elements can also be added to the product before administration to the patient. In such case, said vitamins and/or trace elements are added to the reconstituted solution immediately before the solution is infused into the patient.

According to what is disclosed herein, the above formulation contained in the first and the second chamber of a product for peripheral administration can be mixed or reconstituted by breaking the peelable seal between the chambers. The reconstituted solution for central parenteral nutrition thus comprises, according to one embodiment,

| | |
|---|---|
| 10.8-14.04 g/L | L-Alanine, |
| 6.01-7.80 g/L | L-Arginine, |
| 5.38-6.98 g/L | Glycine, |
| 2.50-3.25 g/L | L-Histidine, |
| 3.13-4.07 g/L | L-Isoleucine, |
| 3.81-4.95 g/L | L-Leucine, |
| 3.03-3.94 g/L | L-Lysine, |
| 2.09-2.71 g/L | L-Methionine, |
| 2.92-3.80 g/L | L-Phenylalanine, |
| 3.55-4.61 g/L | L-Proline, |
| 2.61-3.39 g/L | L-Serine, |
| 2.19-2.85 g/L | L-Threonine, |
| 0.94-1.22 g/L | L-Tryptophan, |
| 0.21-0.27 g/L | L-Tyrosine, |
| 3.03-3.93 g/L | L-Valine, and |
| 4.6-5.4% | dextrose. |

It is one aspect of the present invention to provide for a PN solution for peripheral administration wherein the ratio of the concentration (%) of amino acids to dextrose is about 6:5.

According to another embodiment, the reconstituted solution for peripheral administration comprises only a limited amount of acetate and chloride. According to one embodiment, acetate is contained in an amount of from 50 mEq/L and 55 mEq/L, for example 53 mEq/L. According to another embodiment, chloride is contained in an amount of from 22 mEq/L to 26 mEq/L, for example 24 mEq/L.

All products of the present invention are formulated to accommodate patient populations that require up to 2 grams AA/kg/day while administering lower fluid volumes.

Accordingly, the calorie content of the products is optimized to meet the needs of said patients. Products according to the invention which are optimized for central administration have a calorie content of from 650 Kcal/L to 750 Kcal/L, wherein the calories are derived from both the amino acid and the dextrose formulation.

According to one embodiment, a product for central administration has a calorie content of from 780 Kcal/L to 810 Kcal/L, wherein in a product having a ratio of the concentration (%) of amino acids and dextrose of 8:14, about 470 to 480 Kcal/L are derived from the dextrose formulation and 310 to 330 Kcal/L are derived from the amino acid formulation. For example, a product according to the invention may have a ratio of the concentration of amino acids:dextrose (%) of 8:14 and a calorie content of 797 Kcal/L, wherein 477 Kcal/L are derived from the dextrose and 320 Kcal/L are derived from the amino acids.

According to yet another embodiment of the invention, products for central administration have a total nitrogen content of from about 1290 to 1350 mg/100 mL. According to one such embodiment, products according to the invention for central administration have a total nitrogen content of about 1320 mg/100 mL.

According to another embodiment, a product for central administration has a calorie content of from 640 Kcal/L to 680 Kcal/L, wherein in a product having a ratio of the concentration (%) of amino acids and dextrose of 8:10, about 330 Kcal/L to 350 Kcal/L are derived from the dextrose formulation and 310 to 330 Kcal/L are derived from the amino acid formulation. For example, a product according to the invention may have a ratio of the concentration of amino acids:dextrose (%) of 8:14 and a calorie content of 663 Kcal/L, wherein 343 Kcal/L are derived from the dextrose and 320 Kcal/L are derived from the amino acids.

According to yet another embodiment of the invention, products for peripheral administration have a calorie content of from 380 Kcal/L to 430 Kcal/L and a total nitrogen content of from about 950 to 1030 mg/100 mL. According to one such embodiment, products according to the invention for peripheral administration have a total nitrogen content of about 990 mg/100 mL and a calorie content of about 410 Kcal/L.

The products according to the present invention may additionally encompass a third, fourth or fifth chamber which may comprise a lipid formulation, a trace element formulation and/or a vitamin formulation, respectively. For example, the product may have a third chamber which comprises a lipid formulation. Such lipid formulations are an emulsion of an oil phase, a water phase, and an emulsifier that makes the two phases miscible. In case of lipid emulsions, which are to be used as an injectable emulsion for parenteral nutrition, the emulsion must be an oil-in-water (o/w) emulsion. This means that the oil must reside in the internal (or dispersed) phase, while water is the external (or continuous) phase, as the emulsion must be miscible with blood. Lipid emulsion as disclosed herein must therefore also be substantially free of any suspended solids. Of course, the lipid emulsions may contain further components, including, but not limited to, antioxidants, pH modifiers, isotonic agents, vitamins, trace elements and various combinations thereof. An overview over lipid emulsions, their composition and use is provided, for example, in Driscoll, Journal of Parenteral and Enteral Nutrition 2017, 41, 125-134. Further information on the use of lipid emulsions in parenteral nutrition of intensive care patients is provided, for example, in Calder et al, Intensive Care Medicine, 2010, 36(5), 735-749.

The oil phase of the lipid emulsion which can be combined with the amino acid and glucose formulation according to the invention generally includes polyunsaturated fatty acids, such as long-chain polyunsaturated fatty acids, which may be present as the free acid, as an ionized or salt form of the free acid, and/or in ester form. Suitable esters of the polyunsaturated fatty acids/long-chain polyunsaturated fatty acids include, but are not limited to, alkyl esters (e.g., methyl esters, ethyl esters, propyl esters, or combinations thereof) and triglyceride esters. In some cases, the long-chain polyunsaturated fatty acid has a structure R(C=O)OR', wherein R is an alkenyl group having at least 17 carbon atoms, at least 19 carbon atoms, at least 21 carbon atoms, or at least 23 carbon atoms, and R' is absent, H, a counter ion, an alkyl group (e.g., methyl, ethyl, or propyl), or a glyceryl group (e.g., R(C=O)OR' is a monoglyceride, a diglyceride, or a triglyceride). Polyunsaturated fatty acids for use in the lipid formulations disclosed herein include, but are not limited to, linoleic acid (LA), arachidonic acid (ARA), α-linolenic acid (ALA), eicosapentaenoic acid (EPA), docosahexaenoic acid (DHA), stearidonic acid (SDA), γ-linolenic acid (GLA), dihomo-γ-linolenic acid (DPA), and docosapentaenoic acid (DPA), particularly, DHA, ARA, and EPA, each of which may be present in free acid form, ionized or salt form, alkyl ester form, and/or triglyceride form. In some cases, the polyunsaturated fatty acids and/or long-chain fatty acids are present in triglyceride form.

Typically, the lipid formulation includes about 5% to about 35% by weight of an oil phase based on the total weight of the lipid emulsion. For example, the oil phase of the lipid emulsion is present in an amount of about 8% to 120, of about 10% to about 200, of about 10% to about 150, of about 15% to about 200, of about 12% to about 17%, of about 18% to 22% and/or about 20% by weight based on the total weight of the lipid formulation. The oil phase typically and preferably contains, in various amounts depending on the source of the oil, omega-3 fatty acids. The three types of omega-3 fatty acids involved in human metabolism are α-eicosapentaenoic acid (EPA) and docosahexaenoic acid (DHA), both of which are usually found in marine fish oils and linolenic acid (ALA), commonly found in plant oils.

The oil phase and its components can be derived from a single source or different sources (see, for example, Fell et al, Advances in Nutrition, 2015, 6(5), 600-610. Of the plant oils, currently used sources include, but are not limited to, soybean and olive oil as well as coconut or palm kernel oil (medium-chain triglycerides (MCTs)). Another source are algae, including microalgae such as *Crypthecodinium cohnii* and *Schizochytrium* sp., which in some cases serve as the single source of the long-chain polyunsaturated fatty acid docosahexaenoic acid (DHA). Marine oil used in parenteral lipid emulsions is processed from oily fish primarily found in cold water and including, but not limited to, herring, shad and sardines. However, other marine organisms can be used as an oil source, such as, for example, krill, such as Antarctic krill (*Euphausia superba* Dana). Krill oil, for example, provides for both EPA and DHA, in amounts of up to 35% w/w of the fatty acids. Krill oil as a component of lipid emulsions is considered to have anti-inflammatory properties due to the presence of DHA and EPA and is hypothesized to bind endotoxins (Bonaterra et al: Krill oil-in-water emulsions protects against lipopolysaccharides-induced proinflammatory activation of macrophages in vitro. Marine Drugs (2017), 15:74).

The particular combination of the parenteral nutrition formulation according to the invention is advantageous for critically ill patients, especially the effects of the specific ratio between high nitrogen content and low dextrose content go beyond the mere effect of the individual solution.

The parenteral nutrition solution can be administered as the only nutrition of a patient, or in addition to enteral or oral nutrition.

In addition, electrolytes, trace elements and/or vitamins can be administered separately from the parenteral nutrition solution. However, the electrolytes, trace elements and/or vitamins are usually added to the reconstituted formulation shortly before or upon administration to the patient.

The parenteral nutrition formulation according to the invention can be administered over a period of 1 day to several months to a patient for whom parenteral nutrition is indicated.

EXAMPLES

1. Preparation of the Amino Acid and Dextrose Solution

The different raw materials are weighed based on the tank batch size used.

1.1 Amino Acid Solution

The cleaned and nitrogen flushed mixing tank is filled with a first batch of water for injection. When the required temperature is reached, amino acids, electrolytes and glacial acetic acid, as needed, are added to the tank. Agitation is initiated, and the solution is adjusted to final volume with water for injection. The pH of the solution is measured and if needed adjusted with glacial acetic acid to the required pH. The solution is visually checked to ensure it is a clear solution. The dissolved oxygen and the density of the solution are measured.

1.2 Preparation of Dextrose Solution

The cleaned and nitrogen flushed mixing tank is filled with Water for Injection. When the required temperature is reached dextrose and calcium chloride are added to the tank. Agitation is initiated. The pH of the solution is measured and if needed adjusted with hydrochloric acid 25% to the required pH. The solution is visually checked to ensure it is a clear solution. The dissolved oxygen and the density of the solution are measured.

2. Filtration, Filling, Sealing and Sterilization

During the filling process, the solutions are filtered online through a 0.45 μm filtration membrane. Fill volume is determined gravimetrically and is periodically checked during the filling process to ensure uniformity across the batch. Additionally, dissolved oxygen is measured on the first filled containers. The containers are then sealed.

Each filled and sealed container is placed in an overpouch along with one oxygen absorber. The interior space of the overpouch is flushed with nitrogen to reduce the level of oxygen and the overpouch is heat-sealed. The overpouched bags are placed on sterilizer trays for moist heat sterilization.

The product is terminally sterilized at 121° C. and 2.2 bar using a moist heat sterilization process adapted for 1000 mL and 2000 mL containers. A Steam-Air Mixture process is utilized. The exposure time is adapted to the size of the container.

3. Reconstituted Solutions for Central Parenteral Administration 3.1. Reconstituted Solutions without Electrolytes The properties of two reconstituted formulations for central administration (Tables II and III) are disclosed on the basis of a volume of 100 ml. It should be readily understood that deviations from the given amounts which are in the range of up to 2% are considered to be in the scope of the disclosed examples.

TABLE II

Composition and characteristics of a reconstituted parenteral nutrition solution for central administration essentially comprising amino acids and dextrose.

| Components and Characteristics | | Example 3.1.1 | Example 3.1.2 |
|---|---|---|---|
| | Dextrose Hydrous, USP* (g/100 mL) | 14 | 10 |
| | Amino Acids (g/100 mL) | 8 | 8 |
| | Total Nitrogen (mg/100 mL) | 1320 | 1320 |
| Essential Amino acids (mg/100 mL) | Leucine | 584 | 584 |
| | Isoleucine | 480 | 480 |
| | Valine | 464 | 464 |
| | Lysine (added as the hydrochloride salt) | 464 | 464 |
| | Phenylalanine | 448 | 448 |
| | Histidine | 384 | 384 |
| | Threonine | 336 | 336 |
| | Methionine | 320 | 320 |
| | Tryptophan | 144 | 144 |
| Nonessential Amino acids (mg/100 mL) | Alanine | 1656 | 1656 |
| | Arginine | 920 | 920 |
| | Glycine | 824 | 824 |
| | Proline | 544 | 544 |
| | Serine | 400 | 400 |
| | Tyrosine | 32 | 32 |
| Anion profile (mEq/L) | Acetate | 71 | 71 |
| | Chloride | 32 | 32 |
| | pH (Range) | 6.0 (4.5-7.0) | 6.0 (4.5-7.0) |
| Calorie Content (Kcal/L) | From Dextrose | 477 | 343 |
| | From Amino acids | 320 | 320 |
| | Total (Dextrose and Amino Acids) | 797 | 663 |

*"USP" refers to "United States Pharmacopeia (USP) Reference Standard".

3.2 Reconstituted Solutions with Electrolytes

TABLE III

Composition and characteristics of a reconstituted parenteral nutrition solution for central administration comprising amino acids, dextrose and electrolytes.

| Components and Characteristics | | Example 3.2.1 | Example 3.2.2 |
|---|---|---|---|
| | Dextrose Hydrous, USP* (g/100 mL) | 14 | 10 |
| | Amino Acids (g/100 mL) | 8 | 8 |
| | Total Nitrogen (mg/100 mL) | 1320 | 1320 |
| Essential Amino acids (mg/100 mL) | Leucine | 584 | 584 |
| | Isoleucine | 480 | 480 |
| | Valine | 464 | 464 |
| | Lysine (added as the hydrochloride salt) | 464 | 464 |
| | Phenylalanine | 448 | 448 |
| | Histidine | 384 | 384 |
| | Threonine | 336 | 336 |
| | Methionine | 320 | 320 |
| | Tryptophan | 144 | 144 |
| Nonessential Amino acids (mg/100 mL) | Alanine | 1656 | 1656 |
| | Arginine | 920 | 920 |
| | Glycine | 824 | 824 |
| | Proline | 544 | 544 |
| | Serine | 400 | 400 |
| | Tyrosine | 32 | 32 |
| Electrolytes (mg/100 mL) | Sodium Acetate Trihydrate, USP | 0 | 0 |
| | Dibasic potassium phosphate, USP | 261 | 261 |
| | Sodium Chloride, USP | 205 | 205 |
| | Magnesium Chloride, USP* | 51 | 51 |
| | Calcium Chloride Dihydrate, USP* | 33 | 33 |
| Electrolyte Profile (mEq/L)** | Sodium | 35 | 35 |
| | Potassium | 30 | 30 |
| | Magnesium | 5 | 5 |
| | Calcium | 4.5 (2.2 mmol/L) | 4.5 (2.2 mmol/L) |
| | Acetate± | 83 | 83 |
| | Chloride‡ | 76 | 76 |
| | Phosphate (as HPO4) | 30 (15 mmol/L) | 30 (15 mmol/L) |
| | pH (Range) | 6.0 (4.5-7.0) | 6.0 (4.5-7.0) |
| Calorie Content (Kcal/L) | From Dextrose | 477 | 343 |
| | From Amino Acids | 320 | 320 |
| | Total (Dextrose and Amino Acids) | 797 | 663 |

*"USP" refers to "United States Pharmacopeia (USP) Reference Standard".
**Balanced by ions from amino acids.
±Derived from glacial acetic acid (for pH adjustment) and sodium acetate.
‡Contributed by calcium chloride, lysine HCl, magnesium chloride and sodium chloride.

4. Reconstituted Solutions for Peripheral Administration

The properties of a reconstituted formulations for peripheral administration (Table IV) are disclosed on the basis of a volume of 100 ml. It should be readily understood that deviations from the given amounts which are in the range of up to 2% are considered to be in the scope of the disclosed example.

TABLE IV

Composition and characteristics of a reconstituted parenteral nutrition solution for peripheral administration essentially comprising amino acids and dextrose.

| Components and Characteristics | | Example 4.1 |
|---|---|---|
| | Dextrose Hydrous, USP* (g/100 mL) | 5 |
| | Amino Acids (g/100 mL) | 6 |
| | Total Nitrogen (mg/100 mL) | 990 |
| Essential Amino acids (mg/100 mL) | Leucine | 438 |
| | Isoleucine | 360 |
| | Valine | 348 |
| | Lysine (added as the hydrochloride salt) | 348 |
| | Phenylalanine | 336 |
| | Histidine | 288 |
| | Threonine | 252 |
| | Methionine | 240 |
| | Tryptophan | 108 |
| Nonessential Amino acids (mg/100 mL) | Alanine | 1242 |
| | Arginine | 690 |
| | Glycine | 618 |
| | Proline | 408 |
| | Serine | 300 |
| | Tyrosine | 24 |
| Anion profile (mEq/L) | Acetate | 53 |
| | Chloride | 24 |
| | pH (Range) | 6.0 (4.5-7.0) |
| Calorie Content (Kcal/L) | From Dextrose | 170 |
| | From Amino acids | 240 |
| | Total (Dextrose and Amino Acids) | 410 |

*"USP" refers to "United States Pharmacopeia (USP) Reference Standard".

5. Stability of the Products

Examples having a volume of 2000 mL according to Examples 3.1.1 and 3.1.2 (formulation for central administration without electrolytes) and examples having a volume of 1000 mL according to Examples 3.2.1 and 3.2.2 (formulation for central administration with electrolytes) as well as examples having a volume of 1000 ml according to Example 4.1 (formulation for peripheral administration), see Table V.

TABLE V

Constitution of batches tested for stability

| Example | Ratio of amino acid and dextrose concentration [%] | Electrolytes | Volume tested [mL] | No. of tested batches |
|---|---|---|---|---|
| A | 3.1.1 (cetral) | 8/14 | No | 2000 | 1 |
| B | 3.1.2 (central) | 8/10 | No | 2000 | 2 |
| C | 3.2.1 (central) | 8/14 | Yes | 1000 | 2 |
| D | 3.2.2 (central) | 8/10 | Yes | 1000 | 1 |
| E | 4.1 (peripheral) | 6/5 | No | 1000 | 3 |

The stability of the formulations according to Examples A through E of Table V were studied for for formulations with and without electrolytes to confirm the stability of the product. The formulations have been manufactured at described above (Example 1 and 2). The samples were stored at long term and accelerated storage conditions in controlled climatic rooms with a tolerance of ±2° C. and ±5% relative humidity (RH).

The stability study was conducted with the following conditions:

25° C.±2° C./40% RH±5% RH, with samples tested after 0, 3, 6, 9, 12, 18 and 24 months.

40° C.±2° C./NMT25% RH (regulated at 20% RH±5% RH), with samples tested 3 and 6 months.

It was found that at each time the physicochemical tests (visual inspection, color, pH, extractable volume) gave positive results for all storage conditions for all texted Examples A to E.

The amino acids remained stable and were found in the expected concentration ranges at all storage conditions for all tested Examples A to E. The level of electrolytes (sodium, potassium phosphate dibasic, magnesium, acetate and chloride as NaCl, where applicable) remained stable at all storage conditions for all tested Examples A to E.

The physico-chemical tests (visual inspection, color, pH, extractable volume) gave positive results for all storage conditions for all the tested Examples A to E. The dextrose remained stable at all storage conditions for all the tested Examples A to E.

The mixed solution was also reviewed in each case. The physico-chemical tests (visual inspection, color, pH, particles) confirmed the above results for all the tested examples up to 3 months at long-term conditions 25° C./40% RH and accelerated conditions 40° C./NMT25% RH. No trends were observed over time.

What is claimed is:

1. A sterile medical product for parenteral administration comprising a polymeric container having a first and second chamber which are separated by a non-permanent peel seal, wherein the first chamber contains an amino acid formulation comprising

| | |
|---|---|
| 23.29-28.47 g/L | L-Alanine, |
| 12.94-15.82 g/L | L-Arginine, |
| 11.58-14.16 g/L | Glycine, |
| 5.40-6.60 g/L | L-Histidine, |
| 6.75-8.24 g/L | L-Isoleucine, |
| 8.22-10.04 g/L | L-Leucine, |
| 6.53-7.98 g/L | L-Lysine, |
| 4.50-5.50 g/L | L-Methionine, |
| 6.30-7.70 g/L | L-Phenylalanine, |
| 7.65-9.35 g/L | L-Proline, |
| 5.63-6.88 g/L | L-Serine, |
| 4.72-5.77 g/L | L-Threonine, |
| 2.02-2.47 g/L | L-Tryptophan, |
| 0.45-0.54 g/L | L-Tyrosine, and |
| 6.53-7.98 g/L | L-Valine, | and wherein the second chamber comprises a dextrose formulation having a pH of from 3.2 to 6.5 at 25° C., wherein the dextrose is provided in a concentration of between 26.6% and 41.0%.

2. The medical product according to claim 1, wherein the first chamber further comprises electrolytes comprising sodium, potassium, phosphate, magnesium, acetate, and chloride.

3. The medical product according to claim 2, wherein the electrolytes are present in an amount of from

| | |
|---|---|
| 49.0-60.0 mEq/L | sodium, |
| 3.67-4.49 g/L | potassium phosphate dibasic, |
| 7.0-9.0 mEq/L | magnesium, |
| 103.0-155.0 mEq/L | acetate, and |
| 5.9-7.2 g/L | chloride as NaCl. |

4. The medical product according to claim 1, wherein the second chamber further comprises from 11 to 14 mEq/L calcium.

5. The medical product according to claim 1, wherein the second chamber comprises dextrose in a concentration of from 26.6% to 29.4%.

6. The medical product according to claim 1, wherein the second chamber comprises dextrose in a concentration of from 37.1% to 41.0%.

7. The medical product according to claim 6, wherein the total calorie content of the product is from 780 Kcal/L to 810 Kcal/L.

8. The medical product according to claim 1, wherein the total nitrogen content of the product is from 12.90 g/L to 13.50 g/L.

9. The medical product according to claim 1 for central parenteral nutrition of a patient in need thereof.

10. The medical product according to claim 1, wherein the pH in the first chamber is from 5.0 to 7.0.

11. The medical product according to claim 1, wherein the pH of a solution reconstituted from the formulations contained in the first and the second chambers is from 4.5 to 7.0.

12. The medical product according to claim 1, wherein the non-permanent peel seal between the first and the second chamber is arranged vertically.

13. The medical product according to claim 1, wherein the volume ratio between the first and the second chamber is from 1:1 to 2.0:1.

14. The medical product according to claim 13, wherein the volume ratio is between 1.5:1 and 1.8:1.

15. The medical product according to claim 1, wherein an injection site port tube is located on the second chamber, and an administration site port tube is located on the first chamber.

16. The medical product according to claim 1, wherein the product comprises a third chamber which is separated from the first and/or the second chamber by one or two non-permanent peel seals, and wherein the third chamber comprises a lipid emulsion which upon breaking the one or two non-permanent peel seal(s) can be admixed with the formulation of the first and/or the second chamber before administration.

17. The medical product according to claim 1, wherein the product is terminally moist heat-sterilized.

18. A solution reconstituted from the medical product according to claim 1 for providing parenteral nutrition to a patient whose alimentary tract cannot be used, and/or whose gastrointestinal absorption of protein is impaired, and/or whose metabolic requirements for protein are increased.

* * * * *